US012767966B2

(12) United States Patent
Hong et al.

(10) Patent No.: US 12,767,966 B2
(45) Date of Patent: Oct. 20, 2026

(54) LIPASE MUTANT AND APPLICATION THEREOF

(71) Applicant: ASYMCHEM LIFE SCIENCE (TIANJIN) CO., LTD., Tianjin (CN)

(72) Inventors: Hao Hong, Morrisville, NC (US); Gage James, Morrisville, NC (US); Na Zhang, Tianjin (CN); Xuecheng Jiao, Tianjin (CN); Fang Liu, Tianjin (CN); Ru Jia, Tianjin (CN); Wenjing Liu, Tianjin (CN)

(73) Assignee: ASYMCHEM LIFE SCIENCE (TIANJIN) CO., LTD., Tianjin (CN)

( * ) Notice: Subject to any disclaimer, the term of this patent is extended or adjusted under 35 U.S.C. 154(b) by 278 days.

(21) Appl. No.: 18/691,605

(22) PCT Filed: Oct. 13, 2021

(86) PCT No.: PCT/CN2021/123607
§ 371 (c)(1),
(2) Date: Mar. 13, 2024

(87) PCT Pub. No.: WO2023/035357
PCT Pub. Date: Mar. 16, 2023

(65) Prior Publication Data

US 2024/0401091 A1 Dec. 5, 2024

(30) Foreign Application Priority Data

Sep. 13, 2021 (CN) ......................... 202111065741.4

(51) Int. Cl.

| | |
|---|---|
| ***C12N 9/18*** | (2006.01) |
| ***C12N 15/70*** | (2006.01) |
| ***C12P 7/62*** | (2022.01) |
| *C12R 1/19* | (2006.01) |

(52) U.S. Cl.
CPC .................. *C12P 7/62* (2013.01); *C12N 9/18* (2013.01); *C12N 15/70* (2013.01); *C12R 2001/19* (2021.05); *C12Y 301/01003* (2013.01)

(58) Field of Classification Search
CPC .............. C12P 7/62; C12N 15/70; C12N 9/20
See application file for complete search history.

(56) References Cited

U.S. PATENT DOCUMENTS 6,551,795 B1 * 4/2003 Rubenfield ............ C07K 14/21 435/6.15

FOREIGN PATENT DOCUMENTS

| | | | |
|---|---|---|---|
| CN | 1800401 | A | 7/2006 |
| CN | 106191147 | A | 12/2016 |
| CN | 106459939 | | 2/2017 |
| CN | 111218437 | | 6/2020 |
| CN | 112375751 | A | 2/2021 |
| JP | 6146173 | A | 3/1986 |
| JP | 6146173 | U | 3/1986 |
| JP | 6146173 | B2 | 10/1986 |
| WO | 2021118137 | A1 | 6/2021 |

OTHER PUBLICATIONS

Anonymous, "estA—Esterase—Pseudomonas putida (Arthrobacter siderocapsulatus)," UniProt (2020), Accession No. A0PJ10.
Anonymous, "EstA family serine hydrolase—Pseudomonas putida (Arthrobacter siderocapsulatus)," UniProt (2020), Accession No. A0A177SGG3.
Chen, S. X., et al., "Screening of strain producing an novel esterase with high enantioselectivity and molecular cloning of the enzyme gene," Acta Microbiologica Sinica, vol. 47, No. 3 (2007), pp. 452-455.
Chen, S., et al., "Pseudomonas putida strain NH10 esterase (estA) gene, complete cds," NCBI, GenBank (2009), Accession No. AY896293.
Millar, R., et al., "Esterase EstK from Pseudomonas putida mt-2: An enantioselective acetylesterase with activity for deacetylation of xylan and poly(vinylacetate)," Biotechnology and Applied Biochemistry, vol. 64, No. 6 (2017), pp. 803-809.
Tanyeli, C., et al., "Enzyme catalyzed reverse enantiomeric separation of methyl (+/−)-3-cyclohexene-1-carboxylate," Tetrahedron Asymmetry, vol. 15, No. 13 (2004), pp. 2057-2060.
Wang, J., et al., "Enhancing the atypical esterase promiscuity of the [gamma]-lactamase Sspg from Sulfolobus solfataricus by substrate screening," Applied Microbiology and Biotechnology, vol. 103, No. 10 (Apr. 6, 2019), pp. 4077-4087.
Xu, F., et al., "Discovery and expression of a *Pseudomonas* sp. esterase as a novel biocatalyst for the efficient biosynthesis of a chiral intermediate of pregabalin," Biotechnology and Bioprocess Engineering, vol. 20, No. 3 (2015), pp. 473-487.
Chen Shao-Xin, Shi Bing-Zhao, "Screening of strain producing an novel esterase with high enantioselectivity and molecular cloning of the enzyme gene", Acta Mierobiologica Sinica, vol. 47, No. 3 (2007), pp. 452-455.
Chen, S. X., "esterase [Pseudomonas putida]", Protein, NCBI, GenBank: AAX86642.1 (2009). 1 page.
Wessels, L., "beta-lactamase family protein [Pseudomonas putida]", Protein , NCBI, GenBank: MBF8671915.1 (Nov. 24, 2020) 2 pages.

* cited by examiner

*Primary Examiner* — Tekchand Saidha
(74) *Attorney, Agent, or Firm* — Riverside Law LLP

(57) ABSTRACT

Provided are a lipase mutant and an application thereof. Specifically, one or more mutations selected from A262H, A338V, V364I, A158P/V, and 1159N are generated on the basis of an amino acid sequence as shown in SEQ ID NO: 1; and compared with a parental lipase, a change in the structure and function of a protein occurs in the lipase mutant, and the stereoselectivity is improved, such that a usage amount of an enzyme is decreased to a certain extent, the post-treatment difficulty is reduced, and the lipase mutant is suitable for industrial production.

16 Claims, No Drawings

Specification includes a Sequence Listing.

SEQUENCE LISTING

```
<160> NUMBER OF SEQ ID NOS: 2

<210> SEQ ID NO 1
<211> LENGTH: 381
<212> TYPE: PRT
<213> ORGANISM: Pseudomonas putida

<400> SEQUENCE: 1

Met Gln Ile Gln Gly His Tyr Glu Leu Lys Phe Glu Ala Val Arg Glu
1               5                   10                  15

Thr Phe Ala Ala Leu Phe Asp Asp Pro Gln Glu Arg Gly Ala Ala Leu
            20                  25                  30

Cys Ile Gln Val Gly Gly Glu Thr Val Val Asp Leu Trp Ala Gly Ser
        35                  40                  45

Ala Asp Lys Asp Gly Gln Gln Ala Trp His Ser Asp Thr Ile Ala Asn
    50                  55                  60

Leu Phe Ser Cys Thr Lys Thr Phe Thr Ala Val Thr Ala Leu Gln Leu
65                  70                  75                  80

Val Gly Glu Gly Lys Leu Thr Leu Asp Ala Pro Val Ala Asn Tyr Trp
                85                  90                  95

Pro Glu Phe Ala Gln Ala Gly Lys Gln Ala Ile Thr Leu Arg Gln Leu
            100                 105                 110
```

-continued

```
Leu Ser His Arg Ala Gly Leu Pro Ala Ile Arg Glu Leu Leu Pro Ala
        115                 120                 125

Glu Ala Leu Tyr Asp Trp Gln Ala Met Val Asp Ala Leu Ala Ala Glu
    130                 135                 140

Thr Pro Trp Trp Thr Pro Gly Thr Glu His Gly Tyr Ala Ala Ile Thr
145                 150                 155                 160

Tyr Gly Trp Leu Ile Gly Glu Leu Ile Arg Arg Ala Asp Gly Arg Gly
                165                 170                 175

Pro Gly Asp Ser Ile Val Ala Arg Thr Ala Arg Pro Leu Gly Leu Asp
            180                 185                 190

Phe His Val Gly Leu Ala Asp Asp Glu Phe Tyr Arg Val Ala His Ile
        195                 200                 205

Ala Arg Gly Lys Gly Asn Ala Gly Asp Ala Ala Ala Gln Arg Leu Leu
    210                 215                 220

Gln Val Thr Met Arg Glu Pro Glu Ala Leu Ser Thr Arg Ala Phe Thr
225                 230                 235                 240

Asn Pro Pro Ala Ile Leu Thr Ser Thr Asn Lys Pro Glu Trp Arg Arg
                245                 250                 255

Met Gln Gln Pro Ala Ala Asn Gly His Gly Asn Ala Arg Ser Leu Ala
            260                 265                 270

Gly Phe Tyr Ala Gly Leu Leu Asp Gly Ser Leu Leu Glu Ser Glu Leu
        275                 280                 285

Leu Asp Glu Leu Thr Arg Glu His Ser Leu Gly Gln Asp Arg Thr Leu
    290                 295                 300

Leu Thr Gln Thr Arg Phe Gly Leu Gly Cys Met Leu Asp Gln Pro Asp
305                 310                 315                 320

Val Ala Asn Ala Thr Phe Gly Leu Gly Ala Arg Ala Phe Gly His Pro
                325                 330                 335

Gly Ala Gly Gly Ser Val Gly Phe Ala Asp Pro Glu His Asp Val Ala
            340                 345                 350

Phe Gly Phe Val Val Asn Thr Leu Gly Pro Tyr Val Leu Met Asp Pro
        355                 360                 365

Arg Ala Gln Lys Leu Val Arg Val Leu Ala Ser Cys Leu
    370                 375                 380


<210> SEQ ID NO 2
<211> LENGTH: 1143
<212> TYPE: DNA
<213> ORGANISM: Pseudomonas putida

<400> SEQUENCE: 2

atgcagatcc aaggccacta tgagctgaag ttcgaggcag tgcgcgagac gttcgcagcg      60

ctgttcgacg acccgcaaga gcgtggtgct gcactgtgta tccaggtcgg tggcgaaacc     120

gtagtcgacc tgtgggcagg tagcgcagat aaggacggtc agcaagcgtg gcatagcgac     180

accatcgcaa acctgttctc ctgcaccaaa accttcaccg cggttaccgc tctgcagctg     240

gtgggcgaag gcaaactgac cctggacgcg cctgtggcaa actactggcc agaattcgcg     300

caggcaggta aacaggctat cactctgcgc cagctgctga gccaccgtgc cggtctgcca     360

gcaatccgtg aactgctgcc ggctgaagca ctgtacgact ggcaagcaat ggtggatgcc     420

ctggcagcag aaaccccgtg gtggactccg ggtactgaac atggttacgc cgctattacc     480

tacggctggc tgatcggcga actgatccgt cgtgcggacg gtcgtggtcc tggtgactct     540

attgtggccc gtactgctcg tccgctgggt ctggatttcc atgtcggtct ggccgatgac     600
```

-continued

```
gaattctatc gcgttgcgca cattgcgcgt ggcaaaggca acgcgggcga tgctgcggct    660

cagcgtctgc tgcaggttac tatgcgtgaa ccggaagctc tgtctacccg tgctttcacc    720

aacccgccgg cgattctgac ttccacgaac aaaccggaat ggcgccgtat gcagcagccg    780

gcggctaacg gtcacggtaa tgctcgctct ctggctggtt tttacgcggg tctgctggac    840

ggtagcctgc tggaatctga gctgctggat gaactgacgc gcgaacactc cctgggccag    900

gatcgcaccc tgctgaccca gactcgcttt ggtctgggtt gtatgctgga ccagccggat    960

gttgctaatg ccacgtttgg cctgggcgcg cgtgcgttcg gccacccagg cgcgggcggc   1020

tctgttggct tcgctgatcc ggaacacgat gttgcgtttg gctttgttgt aaacaccctg   1080

ggtccgtatg ttctgatgga tccgcgtgcc cagaaactgg tacgtgtact ggcctcctgc   1140

ctg                                                                 1143
```

LIPASE MUTANT AND APPLICATION THEREOF

CROSS-REFERENCE TO RELATED APPLICATIONS

This application is a U.S. national phase application filed under 35 U.S.C. § 371 claiming benefit to International Patent Application No. PCT/CN2021/123607, filed Oct. 13, 2021, which claims priority to Chinese Patent Application No. 202111065741.4, filed Sep. 13, 2021, the contents of each of which are incorporated by reference herein in their entireties.

REFERENCE TO A "SEQUENCE LISTING," A TABLE, OR A COMPUTER PROGRAM LISTING APPENDIX SUBMITTED AS AN ASCII TEXT FILE

The Sequence Listing written in the ASCII text file: "206418-0029-00US_SequenceListing_ST25.txt"; created on Mar. 12, 2024, and 5,560 bytes in size, is hereby incorporated by reference.

TECHNICAL FIELD

The present disclosure relates to the field of industrial enzymes, in particular to a lipase mutant and an application thereof.

BACKGROUND

At present, methods commonly used in industrial applications of chiral drug synthesis include a chemical catalysis method and an enzymatic catalysis method. The chemical catalysis uses alkali metals as catalysts, it is cheap in price, mature in technologies, and it is relatively easy to produce on a large scale. However, reactions of this method have certain randomness, and have the disadvantages such as poor selectivity, non-specific products, more by-products, and low yield. In comparison, the enzymatic catalysis has the advantages of mild catalytic conditions, green environmental protection, and reduction of reaction by-products. For example, in the resolution of chiral drugs such as acids, alcohols, and esters, chemical methods are commonly used to synthesize racemates of corresponding methyl ester, ethyl ester, or propyl ester, and then lipase or esterase is used for stereoselective hydrolysis to obtain a chiral unit with a single enantiomeric configuration.

The lipase is an enzyme widely present in animals, plants, and microorganisms, and may catalyze reactions such as ammonolysis, alcoholysis, esterification, transesterification, and reverse synthesis of the esters. The commonly used lipase includes a porcine pancreatic lipase, a *Candida* lipase, a *Pseudomonas* lipase, and a *Mucor* lipase (Application of Biocatalyst in Chiral Drug Synthesis [J]. Amino Acids and Biological Resources, 2013, 35 (4): 39-42). For example, invention patent application with publication number of CN 108642025A discloses that 1,3-site selectivity of mutants M8A, L10A, and T9A derived from a *Rhizopus chinensis* lipase is 4.75 times higher than that of wild-type enzymes. This mutant is applied in catalytic reactions of human milk fat substitutes and achieves significant results.

The lipase derived from the microorganisms has the advantages of high stereoselectivity, wide catalytic temperature range, high conversion efficiency, and few by-products and the like. It is commonly used for catalytic chiral resolution, preparation of organic synthesis intermediates such as single chiral alcohols, amines, and esters (Research Progress on Immobilization and Chiral Resolution Thereof of Lipase [J]. Applied Chemistry, 2011, 40 (10): 1823-1827). For example, herbicide (R)-α-phenoxypropyl ester and anti-inflammatory drug (S)-phenylpropanol are all stereoselectively converted into a single active isomer by the lipase.

However, existing commercial lipases have a problem of high cost. In industrial production, especially when a substrate is in the form of the racemates, most of the wild-type lipases have the poor stereoselectivity, so that it is almost impossible to directly obtain the wild-type industrial enzyme that catalyzes a single configuration substrate. In addition, most of the wild-type lipases may have the disadvantages such as low catalytic efficiency and weak stability, so that there are not many lipases that may be widely used truly and have the good stereoselectivity.

SUMMARY

A main purpose of the present disclosure is to provide a lipase mutant and an application thereof, as to solve a problem in existing technologies that the industrial lipase is low in stereoselectivity.

In order to achieve the above purpose, according to an aspect of the present disclosure, a lipase mutant is provided, and the lipase mutant comprises: 1) a protein having the amino acid sequence of SEQ ID NO: 1 with a mutation of one or more amino acids selected from the group consisting of:

| | |
|---|---|
| A262H | |
| A338V | |
| V364I | A262H + A338V + V364I + L65I |
| A158P | A262H + A338V + V364I + P243K |
| A158V | A262H + A338V + V364I + F66Y |
| I159N | A262H + A338V + V364I + A158P + L365Q |
| A262H + A338V | A262H + A338V + V364I + A158P + N263G |
| A262H + A338V + V364I | A262H + A338V + V364I + A158P + C68S |
| A262H + A338V + V364I + A158P | A262H + A338V + V364I + A158P + C68Y |
| A262H + A338V + V364I + A158V | A262H + A338V + V364I + A158P + L365V |
| A262H + A338V + V364I + A158P + I159N | A262H + A338V + V364I + A158P + Y363M |
| A262H + A338V + V364I + A158V + I159N | A262H + A338V + V364I + A158P + P336G |
| A262H + A338F | A262H + A338V + V364I + A158P + S67P |
| A262H + A338L | A262H + A338V + V364I + A158P + V226I |
| A262H + I245W | A262H + A338V + V364I + A158P + V226W |
| A262H + I245H | A262H + A338V + V364I + A158P + T236R |
| A262H + I245S | A262H + A338V + V364I + A158P + L365T |
| A262H + I245C | A262H + A338V + V364I + A158V + L365Q |
| A262H + S67R | A262H + A338V + V364I + A158V + N263G |

-continued

| | |
|---|---|
| A262H + A338V + A158P | A262H + A338V + V364I + A158V + C68S |
| A262H + A338V + A158V | A262H + A338V + V364I + A158V + C68Y |
| A262H + A338V + R123K | A262H + A338V + V364I + A158V + L365V |
| A262H + A338V + H262E | A262H + A338V + V364I + A158V + Y363M |
| A262H + A338V + V364H | A262H + A338V + V364I + A158V + P336G |
| A262H + A338V + R237F | A262H + A338V + V364I + A158V + S67P |
| A262H + A338V + G337A | A262H + A338V + V364I + A158P + L365Q + I159N |
| A262H + A338V + V364L | A262H + A338V + V364I + A158P + N263G + I159N |
| A262H + A338V + T236N | A262H + A338V + V364I + A158P + C68S + I159N |
| A262H + A338V + V364F | A262H + A338V + V364I + A158P + C68Y + I159N |
| A262H + A338V + H262Y | A262H + A338V + V364I + A158P + L365V + I159N |
| A262H + A338V + V364I + I245W | A262H + A338V + V364I + A158P + Y363M + I159N |
| A262H + A338V + V364I + I159Y | A262H + A338V + V364I + A158P + P336G + I159N |
| A262H + A338V + V364I + I159F | A262H + A338V + V364I + A158P + S67P + I159N |
| A262H + A338V + V364I + V364L | A262H + A338V + V364I + A158P + V226I + I159N |
| A262H + A338V + V364I + A244I | A262H + A338V + V364I + A158P + V226W + I159N |
| A262H + A338V + V364I + I245D | A262H + A338V + V364I + A158P + T236R + I159N |
| A262H + A338V + V364I + L65T | A262H + A338V + V364I + A158P + L365T + I159N |
| A262H + A338V + V364I + T160L | A262H + A338F + V364I |
| A262H + A338V + V364I + P243M | A262H + A338L + V364I |

or 2) a protein has the mutation of the protein in 1) and has an amino acid sequence with more than 80% identity to the amino acid sequence of the protein in 1), and the lipase mutant is derived from *Pseudomonas putida* and has the lipase activity.

Further, the protein in 2) has an amino acid sequence with more than 90%, preferably more than 95%, and more preferably more than 99% identity to the amino acid sequence of the protein in 1), and the lipase mutant is derived from *Pseudomonas putida* and has the lipase activity.

In order to achieve the above purpose, according to a second aspect of the present disclosure, a DNA molecule is provided, and encodes the above lipase mutant.

According to a third aspect of the present disclosure, a recombinant plasmid is provided, and the recombinant plasmid comprises the above DNA molecule.

Further, the recombinant plasmid is selected from any one of the following: pET-21b(+), pET-22b(+), pET-3a(+), pET-3d(+), pET-11a(+), pET-12a(+), pET-14b, pET-15b(+), pET-16b(+), pET-17b(+), pET-19b(+), pET-20b(+), pET-21a(+), pET-23a(+), pET-23b(+), pET-24a(+), pET-25b(+), pET-26b(+), pET-27b(+), pET-28a(+), pET-29a(+), pET-30a(+), pET-31b(+), pET-32a(+), pET-35b(+), pET-38b(+), pET-39b(+), pET-40b(+), pET-41a(+), pET-41b(+), pET-42a(+), pET-43a(+), pET-43b(+), pET-44a(+), pET-49b(+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwin1, pEZZ18, pKK232-8, pUC-18 and pUC-19.

According to a fourth aspect of the present disclosure, a non-plant host cell is provided, and the host cell contains any one of the above recombinant plasmids.

Further, the host cell is a prokaryotic cell or a eukaryotic cell, and the eukaryotic cell is a yeast cell.

Further, the host cell is a competent cell.

Further, the competent cell is an *Escherichia coli* BL21 cell or an *Escherichia coli* W3110 cell.

According to a fifth aspect of the present disclosure, a preparation method for a chiral compound is provided, and the preparation method includes: any one of the above lipase mutants is used to catalyze hydrolysis of an ester compound shown in Formula I into an acid compound shown in Formula II and an alcohol compound shown in Formula III:

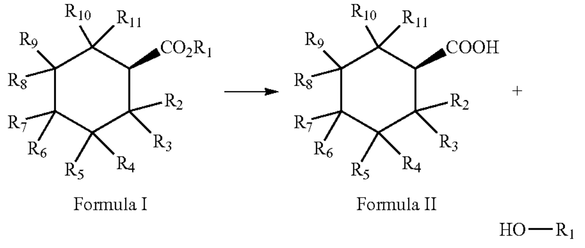

Formula I

Formula II

Formula III

Herein, $R_1$ is selected from any one of the following: $CH_3$, $CH_2CH_3$, $CH_2—CH_2CH_3$, or $CHCH_3CH_3$.

$R_2$, $R_3$, $R_4$, and $R_5$ are each independently selected from any one of the following: H, F, Cl, Br, I, OH, $CH_3$, or $CH_2CH_3$.

The presence or absence of a double bond in a cyclohexane ring, when it is present, the double bond forms at any one or more of the following sites: between $R_3$ and $R_4$, between $R_5$ and $R_6$, between $R_7$ and $R_8$, and between $R_9$ and $R_{10}$.

Further, the ester compound is any one of the following:

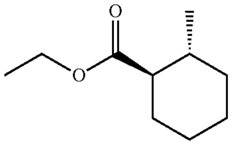,

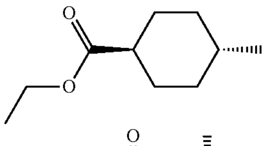,

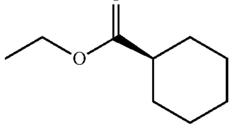,

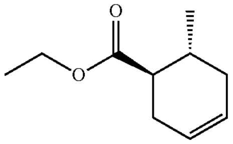,

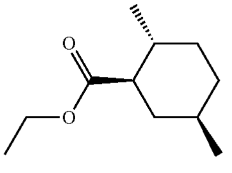 and

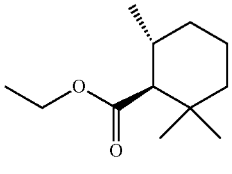.

Further, the lipase mutant catalyzes a hydrolysis reaction of the ester compound shown in Formula I at a temperature of 15° C.~30° C.

Further, a mass ratio of a bacterial sludge amount of the lipase mutant to the ester compound is 1:10~1:1.

Further, a reaction system also contains an organic solvent, and the organic solvent is selected from any one of the following: dimethylsulfoxide (DMSO), acetone, dimethyltetrahydrofuran, isopropanol, and n-propanol.

Further, a volume percentage content of the organic solvent in the reaction system is 5%~10%.

By applying technical schemes of the present disclosure, the lipase mutant is obtained by rational design and a plurality of rounds of evolution screening for enzymes based on the amino acid sequence shown in SEQ ID NO: 1. Compared with the female parent lipase, the protein structure and function of the lipase mutant are changed. In practical applications, the stereoselectivity of the lipase mutant is greatly improved. In addition, the increase in stereoselectivity of the lipase mutant reduces the usage amount of the enzyme to a certain extent, the post-treatment difficulty is reduced, and the lipase mutant is suitable for industrial production.

DETAILED DESCRIPTION OF THE EMBODIMENTS

It should be noted that in the case without conflicting, embodiments in the present application and features in the embodiments may be combined with each other. The present disclosure is described in detail below in combination with the embodiments.

As mentioned in the background, the industrial lipases in the prior art have the relatively low stereoselectivity. In order to improve this situation, the present disclosure obtains a series of lipase mutants with improved stereoselectivity by rational design and a plurality of rounds of evolution screening for enzymes. On basis of this, the applicant provides the scheme of the present application.

In a typical embodiment, a lipase mutant is provided, and the amino acid sequence of the lipase mutant is obtained by the following mutations of the amino acid sequence shown in SEQ ID NO: 1:

| | |
|---|---|
| A262H | |
| A338V | |
| V364I | |
| A158P | A262H + A338V + V364I + P243K |
| A158V | A262H + A338V + V364I + F66Y |
| I159N | A262H + A338V + V364I + A158P + L365Q |
| A262H + A338V | A262H + A338V + V364I + A158P + N263G |
| A262H + A338V + V364I | A262H + A338V + V364I + A158P + C68S |
| A262H + A338V + V364I + A158P | A262H + A338V + V364I + A158P + C68Y |
| A262H + A338V + V364I + A158V | A262H + A338V + V364I + A158P + L365V |
| A262H + A338V + V364I + A158P + I159N | A262H + A338V + V364I + A158P + Y363M |
| A262H + A338V + V364I + A158V + I159N | A262H + A338V + V364I + A158P + P336G |
| A262H + A338F | A262H + A338V + V364I + A158P + S67P |
| A262H + A338L | A262H + A338V + V364I + A158P + V226I |
| A262H + I245W | A262H + A338V + V364I + A158P + V226W |
| A262H + I245H | A262H + A338V + V364I + A158P + T236R |
| A262H + I245S | A262H + A338V + V364I + A158P + L365T |
| A262H + I245C | A262H + A338V + V364I + A158V + L365Q |
| A262H + S67R | A262H + A338V + V364I + A158V + N263G |
| A262H + A338V + A158P | A262H + A338V + V364I + A158V + C68S |
| A262H + A338V + A158V | A262H + A338V + V364I + A158V + C68Y |
| A262H + A338V + R123K | A262H + A338V + V364I + A158V + L365V |
| A262H + A338V + H262E | A262H + A338V + V364I + A158V + Y363M |
| A262H + A338V + V364H | A262H + A338V + V364I + A158V + P336G |
| A262H + A338V + R237F | A262H + A338V + V364I + A158V + S67P |
| A262H + A338V + G337A | A262H + A338V + V364I + A158P + L365Q + I159N |
| A262H + A338V + V364L | A262H + A338V + V364I + A158P + N263G + I159N |
| A262H + A338V + T236N | A262H + A338V + V364I + A158P + C68S + I159N |
| A262H + A338V + V364F | A262H + A338V + V364I + A158P + C68Y + I159N |
| A262H + A338V + H262Y | A262H + A338V + V364I + A158P + L365V + I159N |
| A262H + A338V + V364I + I245W | A262H + A338V + V364I + A158P + Y363M + I159N |
| A262H + A338V + V364I + I159Y | A262H + A338V + V364I + A158P + P336G + I159N |
| A262H + A338V + V364I + I159F | A262H + A338V + V364I + A158P + S67P + I159N |
| A262H + A338V + V364I + V364L | A262H + A338V + V364I + A158P + V226I + I159N |
| A262H + A338V + V364I + A244I | A262H + A338V + V364I + A158P + V226W + I159N |
| A262H + A338V + V364I + I245D | A262H + A338V + V364I + A158P + T236R + I159N |
| A262H + A338V + V364I + L65T | A262H + A338V + V364I + A158P + L365T + I159N |
| A262H + A338V + V364I + T160L | A262H + A338F + V364I |
| A262H + A338V + V364I + P243M | A262H + A338L + V364I |

Alternatively, the amino acid sequence of the lipase mutant has the above mutation site(s) and has more than 80% (preferably more than 90%, or more than 95%, or more than 99%, or more than 99.95%, or even more than 99.99%) of identity with the above mutated amino acid sequence, and at the same time, it is derived from *Pseudomonas putida* (namely from the same species as the mutant in the above table) and has the lipase activity.

The amino acid sequence of the above lipase mutant is obtained by a mutation of the amino acid sequence shown in SEQ ID NO: 1. The important site involved in the mutation includes but not limited to one or more of the following sites: A262, A338, V364, A158, I159, I245, L65, F66, S67, C68, R123, T160, V226, L234, T236, R237, P243, A244, N263, H335, P336, G337, Y363 and L365.

It should be noted that the inventor screens more than 100 wild-type lipases from different species to catalyze this type of the substrates (such as Substrate 1), and it is found that the enantiomeric excess (e.e.) values of catalytic selectivity are all very low (<5%), while the lipase of SEQ ID NO: 1 (from *Pseudomonas putida*) has the best e.e. value for the catalytic reaction. Nevertheless, its e.e. value is still not ideal, so it is selected to evolve based on the lipase of SEQ ID NO: 1.

The above lipase mutant is obtained by rational design and a plurality of rounds of evolution screening for enzymes based on the amino acid sequence shown in SEQ ID NO: 1, and changes in protein structure and function are achieved. In practical applications, the stereoselectivity of the lipase mutant is greatly improved. In addition, the increase in stereoselectivity of the lipase mutant reduces the usage amount of the enzyme to a certain extent, the post-treatment difficulty is reduced, and the lipase mutant is suitable for industrial production.

The amino acid sequence of SEQ ID NO: 1 is specifically as follows:

```
MQIQGHYELKFEAVRETFAALFDDPQERGAALCIQVGGETVVDLWAGSA

DKDGQQAWHSDTIANLFSCTKTFTAVTALQLVGEGKLTLDAPVANYWPE

FAQAGKQAITLRQLLSHRAGLPAIRELLPAEALYDWQAMVDALAAETPW

WTPGTEHGYAAITYGWLIGELIRRADGRGPGDSIVARTARPLGLDFHVG

LADDEFYRVAHIARGKGNAGDAAAQRLLQVTMREPEALSTRAFTNPPAI

LTSTNKPEWRRMQQPAANGHGNARSLAGFYAGLLDGSLLESELLDELTR

EHSLGQDRTLLTQTRFGLGCMLDQPDVANATFGLGARAFGHPGAGGSVG

FADPEHDVAFGFVVNTLGPYVLMDPRAQKLVRVLASCL.
```

The corresponding nucleic acid sequence of SEQ ID NO: 2 is as follows:

```
atgcagatccaaggccactatgagctgaagttcgaggcagtgcgcgaga

cgttcgcagcgctgttcgacgacccgcaagagcgtggtgctgcactgtg

tatccaggtcggtggcgaaaccgtagtcgacctgtgggcaggtagcgca

gataaggacggtcagcaagcgtggcatagcgacaccatcgcaaacctgt

tctcctgcaccaaaaccttcaccgcggttaccgctctgcagctggtggg

cgaaggcaaactgaccctggacgcgcctgtggcaaactactggccagaa

ttcgcgcaggcaggtaaacaggctatcactctgcgccagctgctgagcc

accgtgccggtctgccagcaatccgtgaactgctgccggctgaagcact

gtacgactggcaagcaatggtggatgccctggcagcagaaaccccgtgg

tggactccgggtactgaacatggttacgccgctattacctacggctggc

tgatcggcgaactgatccgtcgtgcggacggtcgtggtcctggtgactc

tattgtggcccgtactgctcgtccgctgggtctggatttccatgtcggt

ctggccgatgacgaattctatcgcgttgcgcacattgcgcgtggcaaag

gcaacgcgggcgatgctgcggctcagcgtctgctgcaggttactatgcg

tgaaccggaagctctgtctacccgtgctttcaccaacccgccggcgatt

ctgacttccacgaacaaaccggaatggcgccgtatgcagcagccggcgg

ctaacggtcacggtaatgctcgctctctggctggtttttacgcgggtct

gctggacggtagcctgctggaatctgagctgctggatgaactgacgcgc

gaacactccctgggccaggatcgcaccctgctgacccagactcgctttg

gtctgggttgtatgctggaccagccggatgttgctaatgccacgtttgg

cctgggcgcgcgtgcgttcggccacccaggcgcgggcggctctgttggc
```

-continued

```
ttcgctgatccggaacacgatgttgcgtttggctttgttgtaaacaccc

tgggtccgtatgttctgatggatccgcgtgcccagaaactggtacgtgt

actggcctcctgcctg.
```

Specific methods or steps for the rational design and enzyme evolution screening mentioned above include but are not limited to the following examples:

Firstly, a mutation site is introduced on SEQ ID NO: 1 by a mode of a full-plasmid polymerase chain reaction (PCR), to detect the activity and selectivity of the mutant, and select the mutant with the improved activity and selectivity.

The sequence SEQ ID NO: 1 is used as a template, to design a site-specific mutation primer, and a site-specific mutation means is used, to obtain a mutant plasmid with a target gene by using pET-22b(+) as an expression vector.

Herein, site-specific mutation: refers to introduction of a change (usually the change representing a favorable direction) required into a target DNA fragment (it may be a genome or a plasmid) by methods such as a polymerase chain reaction (PCR), including addition, deletion, and point mutation of bases. The site-specific mutation may quickly and efficiently improve the characters and representation of the target protein expressed by DNA, and is a very useful tool in gene research work.

The method of introducing the site-specific mutation using the full-plasmid PCR is simple and effective, and is a means currently used widely. Its principle is that: a pair of primers (forward and reverse) containing mutation sites and a template plasmid are annealed, and "cyclically extended" with a polymerase. The so-called cyclic extension refers to a cycle that the polymerase extends the primer according to the template, terminates at a 5'-end of the primer after one circle, and then undergoes repeated heating and annealing extension. This reaction is different from rolling circle amplification, and does not form a plurality of tandem copies. Extension products of the forward and reverse primers are annealed, and paired to form an open-loop plasmid with a notch. An extension product of Dpn I enzyme digestion is shredded because the original template plasmid is derived from conventional *Escherichia coli*, modified by dam methylation and sensitive to Dpn I. However, the plasmid with the mutated sequence synthesized in vitro is not cleaved due to the lack of methylation, so it is successfully transformed in subsequent transformations, to obtain a clone of the mutated plasmid.

On the basis of acquiring the mutant with the improved characters by a single site mutation, beneficial amino acid sites may be combined, to obtain the mutant with the better characters.

After the lipase mutant with the significantly improved activity and enantioselectivity is obtained, it is randomly mutated using an error prone PCR, to construct a high-quality mutant library. A suitable high-throughput screening method is developed to screen the library and obtain the mutant with the further improved stereoselectivity.

The error prone PCR: refers to PCR under error prone conditions, namely a PCR technology that may easily cause errors in the replicated DNA sequence, also known as a mismatch PCR or an error tendency PCR. Specifically, it refers to a method of inducing a DNA sequence variation in vitro by using a low fidelity TaqDNA polymerase and changing a PCR reaction condition to reduce the fidelity of DNA replication, increase base mismatch in the synthesis process of a new DNA chain, and thus cause more point mutations in an amplified product.

The error prone PCR is currently the simplest and most effective gene in vitro random mutation technology, and its principle is that: the isomerization of bases provides the possibility of mismatch, and all 4 bases that constitute DNA have tautomers, herein, 3 oxygen-containing bases of guanine (G), cytosine (C), and thymine (T) have two tautomers: keto and enol. Two nitrogen-containing bases of adenine (A) and thymine have two tautomers: amine and imine. G. C and T mainly exist in keto structures, while the ratio of enol structures is extremely low. Nitrogen atoms on the nitrogen-containing bases A and T mainly exist in the amino ($NH_2$) state, while the ratio of imido (NH) state is extremely low. The different positions of hydrogen atoms between different isomers and the different deviation directions of electron clouds at the same position may cause changes in the pairing form of the bases, and this may result in the mismatch on a replicated sub-chain. For example, when the thymine exists in the keto structure, it pairs with the adenine, and while it exists in the enol structure, it pairs with the guanine, this generates an unstable base pair that A may pair with C and T may pair with G, thereby the mismatch is caused.

In a plurality of known heat-resistant DNA polymerase enzymes, Taq DNA polymerase has the highest mismatch rate. Taq DNA polymerase is one of the discovered heat-resistant DNA polymerases with the highest activity, has 5'-3' exonuclease activity and does not have 3'-5' exonuclease activity. Therefore, it does not have a proofreading function for certain single nucleotide mismatches during synthesis, so the probability of mismatches is higher than that of the DNA polymerase with 3'-5' proofreading activity. The fidelity of the DNA polymerase may be reduced by various methods, including using 4 different concentrations of dNTP, adding $Mn^{2+}$, and increasing $Mg^{2+}$ concentration and the like. The mechanisms by which a plurality of mutagenic methods leads to amplification of DNA chain base variations are different. $MnCl_2$ is a mutagen of the DNA polymerase, and the addition of $Mn^{2+}$ may reduce the specificity of the polymerase to the template and increase the mismatch rate; the imbalance of 4 dNTPs concentrations may increase the probability of base misdoping and achieve the mismatch; $Mg^{2+}$ has a function of activating Taq enzyme, the concentration of $Mg^{2+}$ is increased so that it exceeds a normal amount, a non-complementary base pair may be stabilized; increasing the amount of Taq DNA polymerase and increasing the extension time of each cycle may increase the probability of mismatched terminal extension; and reducing the initial template concentration may increase the proportion of a mutated template in the subsequent PCR cycle.

By screening the mutant library constructed by the error prone PCR, the lipase mutant with the further improved activity and enantioselectivity is obtained. A saturated mutation primer is also designed to further evolve the mutant, as to obtain the mutant with the significantly improved activity and enantiomeric stereoselectivity.

The saturation mutation is a method of acquiring a mutant with a target amino acid substituted by 19 other amino acids in a short period of time by modifying a coding gene of a target protein. This method is not only a powerful tool for protein directed modification, but also an important means for researching a protein structure-function relationship. The saturation mutation often obtains a more ideal evolutionary body than the single point mutation. In addition, for these problems that may not be solved by the site-specific mutation method, it is precisely the unique advantage of the saturation mutation method.

The above mutant plasmid is transformed into the *Escherichia coli* cells, and overexpressed in the *Escherichia coli* cells. Then, a crude enzyme is obtained by a method of ultrasionic cell-breaking. The optimal conditions for lipase induced expression are as follows: 0.06 mM isopropyl-β-d-thiogalactoside (IPTG), and induced expression at 20° C. for 16 h.

The mutant selected in the present application undergoes extensive experimental verification, and in the case that a substrate existing in the form of a racemate is not excessively converted, it is ultimately proved that the stereoselectivity of an S-type product of the enzyme catalyzed reaction is significantly improved (such as enantiomeric excess (e.e.) increased from <5% initially to at least 80% or more, and the needs of industrial production are satisfied to a great extent.

In a typical implementation mode of the present disclosure, a DNA molecule is further provided, and the DNA molecule encodes any one of the above lipase mutant. The above lipase mutant encoded has the advantage of high selectivity.

In a typical implementation mode of the present disclosure, a recombinant plasmid is further provided, and the recombinant plasmid is linked to the above DNA molecule. The DNA molecule may encode any one of the above lipase mutants with the high selective. The specific sequence is selected from sequences in Tables 1-5 or nucleotide sequences that undergo substitution, addition, or deletion mutations in amino acid sequences in other sites under the premise of maintaining the above amino acid site changes with these sequences.

In the above recombinant plasmids, any recombinant plasmids that may be used to express the DNA molecule of the above lipase are applicable to the present disclosure. In a preferred implementation mode of the present disclosure, the recombinant plasmid is selected from one of the following: pET-22b(+), pET-21b(+), pET-3a(+), pET-3d(+), pET-11a(+), pET-12a(+), pET-14b, pET-15b(+), pET-16b(+), pET-17b(+), pET-19b(+), pET-20b(+), pET-21a(+), pET-23a(+), pET-23b(+), pET-24a(+), pET-25b(+), pET-26b(+), pET-27b(+), pET-28a(+), pET-29a(+), pET-30a(+), pET-31b(+), pET-32a(+), pET-35b(+), pET-38b(+), pET-39b(+), pET-40b(+), pET-41a(+), pET-41b(+), pET-42a(+), pET-43a(+), pET-43b(+), pET-44a(+), pET-49b(+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwin1, pEZZ18, pKK232-8, pUC-18, and pUC-19.

In a typical implementation mode of the present disclosure, a non-plant host cell is further provided, and the host cell contains any one of the above recombinant plasmids. The specific host cell may a prokaryotic cell or a eukaryotic cell, and preferably the eukaryotic cell is a yeast cell. More preferably, the above host cell is a competent cell, and further preferably the competent cell is an *Escherichia coli* BL21 cell or an *Escherichia coli* W3110 cell.

In a typical implementation mode of the present disclosure, a preparation method for a chiral compound is further provided, and the preparation method includes: any one of the above lipase mutants is used to catalyze hydrolysis of an ester compound shown in Formula I into an acid compound shown in Formula II and an alcohol compound shown in Formula III:

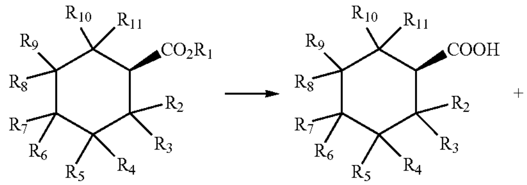

Formula I Formula II $HO-R_1$

Formula III

Herein, $R_1$ is selected from any one of the following: $CH_3$, $CH_2CH_3$, $CH_2—CH_2CH_3$, or $CHCH_3CH_3$, $R_2$, $R_3$, $R_4$, and $R_5$ are each independently selected from any one of the following: H, F, Cl, Br, I, OH, $CH_3$, or $CH_2CH_3$, the presence or absence of a double bond in a cyclohexane ring, when it is present, the double bond forms at any one or more of the following sites: between $R_3$ and $R_4$, between $R_5$ and $R_6$, between $R_7$ and $R_8$, and between $R_9$ and $R_{10}$.

In a preferred embodiment, the ester compound is any one of the following:

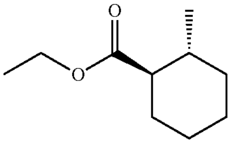,

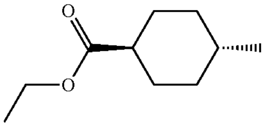,

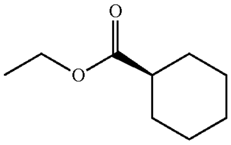,

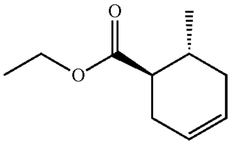,

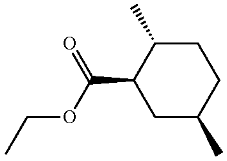 and

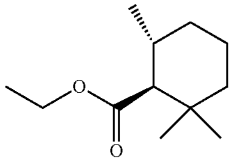.

In a preferred embodiment, the lipase mutant catalyzes a hydrolysis reaction of the ester compound shown in Formula I at a temperature of 15° C.~30° C.

In a preferred embodiment, a mass ratio of a bacterial sludge amount of the lipase mutant to the ester compound is 1:10~1:1. The transformation efficiencies of the different mutants are different, and the mass ratios used are also different when the same transformation e.e. value is reached.

In a preferred embodiment, a reaction system also contains an organic solvent, and the organic solvent is selected from any one of the following: dimethylsulfoxide (DMSO), acetone, dimethyltetrahydrofuran, isopropanol, and n-propanol.

In a preferred embodiment, a volume percentage content of the organic solvent in the reaction system is 5%~10%, and the mutant of the present application still has the relatively high stereoselectivity while the volume percentage content of the organic solvent is within this range.

The beneficial effects of the present application are further described below in combination with specific embodiments. It should be noted that substrates used in the following embodiments include:

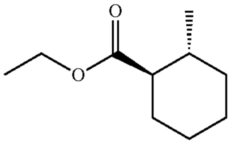

Substrate 1

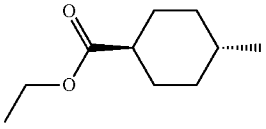

Substrate 2

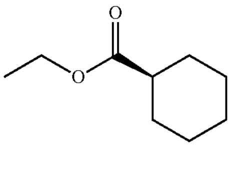

Substrate 3

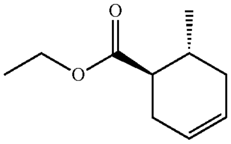

Substrate 4

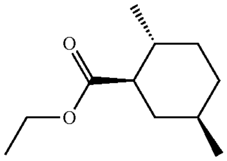

Substrate 5

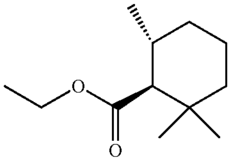

Substrate 6

Embodiment 1

10 mg of Substrate 1/Substrate 2/Substrate 3 were taken respectively, and 1 mg of resuspended lipase or its mutant bacterial sludge was added to a reaction system, 0.3 M pH 7.5 KPB Buffer (54.91 g of $K_2HPO_4·3H_2O$ and 8.08 g of $KH_2PO_4$, were dissolved in 0.9 L of ultrapure water added, and the volume was fixed to 1 L after pH was adjusted to 7.5) was supplemented to 1000 μL of the system, and it was reacted at a constant temperature of 30° C. for 1 h at 200 rpm. 60 μL of 6 M diluted hydrochloric acid was added to the system and the reaction was terminated after being mixed uniformly, then 1 mL of n-hexane was added for extraction, it was shaken fully, and centrifuged at 12000 rpm for 2 min, and an upper layer was taken and sent to a sample bottle for detecting the e.e. value of an S-type product by a normal phase high performance liquid chromatography (HPLC). The response characteristics of some mutants were shown in Table 1:

TABLE 1

| | Selectivity | | |
|---|---|---|---|
| Mutant | Substrate 1 | Substrate 2 | Substrate 3 |
| Female parent | — | — | — |
| A262H | * | ** | ** |
| A338V | ** | ** | ** |
| V364I | ** | ** | * |
| A158P | ** | — | * |
| A158V | ** | * | ** |
| I159N | — | ** | ** |

The selectivity e.e. of the S-type product was represented by *, and the selectivity of the female parent and its equivalent mutant was represented by "—", and it was 0-5%.
* represented that e.e. was 5-10%,
** represented that e.e. was 15%-20%,
*** represented that e.e. was 20-50%,
**** represented that e.e. was 50-80%, and
***** represented that e.e. was ≥80%.

Embodiment 2

10 mg of Substrate 1 and Substrate 4 were taken respectively, and 1 mg of resuspended lipase or its mutant bacterial sludge was added to a reaction system, 0.3 M pH 7.5 KPB Buffer was supplemented to 1000 μL of the system, and it was reacted at a constant temperature of 30° C. for 1 h at 200 rpm. 60 μL of 6 M diluted hydrochloric acid was added to the system and the reaction was terminated after being mixed uniformly, then 1 mL of n-hexane was added for extraction, it was shaken fully, and centrifuged at 12000 rpm for 2 min, and an upper layer was taken and sent to a sample bottle for detecting the e.e. value of an S-type product by a normal phase HPLC. The response characteristics of some mutants were shown in Table 2:

TABLE 2

| | Selectivity | |
|---|---|---|
| Mutant | Substrate 1 | Substrate 4 |
| Female parent | — | — |
| A262H | * | ** |
| A262H + A338V | *** | ** |
| A262H + A338V + V364I | **** | *** |
| A262H + A338V + V364I + A158P | **** | *** |
| A262H + A338V + V364I + A158V | *** | **** |
| A262H + A338V + V364I + A158P + I159N | ***** | **** |
| A262H + A338V + V364I + A158V + I159N | ***** | ***** |
| A262H + A338F | ** | ** |
| A262H + A338L | *** | ** |
| A262H + I245W | ** | ** |
| A262H + I245H | ** | ** |
| A262H + I245S | ** | ** |
| A262H + I245C | ** | ** |
| A262H + S67R | ** | ** |
| A262H + A338V + A158P | *** | *** |
| A262H + A338V + A158V | *** | *** |
| A262H + A338V + R123K | ** | ** |
| A262H + A338V + H262E | ** | *** |
| A262H + A338V + V364H | *** | ** |
| A262H + A338V + R237F | ** | ** |
| A262H + A338V + G337A | ** | *** |
| A262H + A338V + V364L | *** | *** |
| A262H + A338V + T236N | *** | ** |
| A262H + A338V + V364F | ** | *** |
| A262H + A338V + H262Y | ** | ** |
| A262H + A338V + V364I + I245W | **** | *** |
| A262H + A338V + V364I + I159Y | **** | **** |
| A262H + A338V + V364I + I159F | *** | *** |
| A262H + A338V + V364I + V364L | **** | *** |
| A262H + A338V + V364I + A244I | *** | *** |
| A262H + A338V + V364I + I245D | *** | **** |
| A262H + A338V + V364I + L65T | **** | *** |
| A262H + A338V + V364I + T160L | **** | *** |
| A262H + A338V + V364I + P243M | *** | **** |
| A262H + A338V + V364I + L65I | *** | *** |
| A262H + A338V + V364I + P243K | *** | **** |
| A262H + A338V + V364I + F66Y | **** | ** |
| A262H + A338V + V364I + A158P + L365Q | **** | **** |
| A262H + A338V + V364I + A158P + N263G | *** | *** |
| A262H + A338V + V364I + A158P + C68S | *** | **** |
| A262H + A338V + V364I + A158P + C68Y | *** | **** |
| A262H + A338V + V364I + A158P + L365V | **** | *** |
| A262H + A338V + V364I + A158P + Y363M | **** | *** |
| A262H + A338V + V364I + A158P + P336G | **** | *** |
| A262H + A338V + V364I + A158P + S67P | *** | *** |
| A262H + A338V + V364I + A158P + V226I | *** | **** |
| A262H + A338V + V364I + A158P + V226W | *** | **** |
| A262H + A338V + V364I + A158P + T236R | **** | *** |
| A262H + A338V + V364I + A158P + L365T | **** | *** |
| A262H + A338V + V364I + A158V + L365Q | **** | *** |
| A262H + A338V + V364I + A158V + N263G | **** | *** |
| A262H + A338V + V364I + A158V + C68S | **** | **** |

TABLE 2-continued

| Mutant | Selectivity | |
|---|---|---|
| | Substrate 1 | Substrate 4 |
| A262H + A338V + V364I + A158V + C68Y | *** | *** |
| A262H + A338V + V364I + A158V + L365V | *** | **** |
| A262H + A338V + V364I + A158V + Y363M | *** | **** |
| A262H + A338V + V364I + A158V + P336G | **** | *** |
| A262H + A338V + V364I + A158V + S67P | **** | *** |
| A262H + A338V + V364I + A158P + L365Q + I159N | **** | **** |
| A262H + A338V + V364I + A158P + N263G + I159N | **** | *** |
| A262H + A338V + V364I + A158P + C68S + I159N | *** | **** |
| A262H + A338V + V364I + A158P + C68Y + I159N | *** | *** |
| A262H + A338V + V364I + A158P + L365V + I159N | ***** | **** |
| A262H + A338V + V364I + A158P + Y363M + I159N | **** | ***** |
| A262H + A338V + V364I + A158P + P336G + I159N | ***** | ***** |
| A262H + A338V + V364I + A158P + S67P + I159N | **** | **** |
| A262H + A338V + V364I + A158P + V226I + I159N | ***** | ***** |
| A262H + A338V + V364I + A158P + V226W + I159N | ***** | **** |
| A262H + A338V + V364I + A158P + T236R + I159N | ***** | **** |
| A262H + A338V + V364I + A158P + L365T + I159N | ***** | ***** |

The selectivity e.e. of the S-type product was represented by *, and "—" represented that the selectivity of the female parent was 0-5%.
* represented that e.e. was 5-10%,
** represented that e.e. was 15%-20%,
*** represented that e.e. was 20-50%,
**** represented that e.e. was 50-80%, and
***** represented that e.e. was ≥80%.

Embodiment 3

10 mg of Substrate 1/Substrate 2/Substrate 3/Substrate 4/Substrate 5/Substrate 6 were taken respectively, and 1 mg of resuspended lipase or its mutant bacterial sludge was added to a reaction system, 0.3 M pH 7.5 KPB Buffer was supplemented to 1000 μL of the system, and it was reacted at a constant temperature of 30° C. for 1 h at 200 rpm. 60 μL of 6 M diluted hydrochloric acid was added to the system and the reaction was terminated after being mixed uniformly, then 1 mL of n-hexane was added for extraction, it was shaken fully, and centrifuged at 12000 rpm for 2 min, and an upper layer was taken and sent to a sample bottle for detecting the e.e. value of an S-type product by a normal phase HPLC. The response characteristics of some mutants were shown in Table 3:

TABLE 3

| Mutant | Selectivity | | | | | |
|---|---|---|---|---|---|---|
| | Substrate 1 | Substrate 2 | Substrate 3 | Substrate 4 | Substrate 5 | Substrate 6 |
| Female parent | — | — | — | — | — | — |
| A262H | * | ** | ** | ** | — | ** |
| A262H + A338V | *** | ** | *** | ** | *** | * |
| A262H + A338F | ** | *** | ** | ** | ** | ** |
| A262H + A338L | *** | ** | ** | ** | ** | ** |
| A262H + A338V + V364I | **** | *** | **** | *** | *** | ** |
| A262H + A338F + V364I | *** | **** | *** | *** | *** | *** |
| A262H + A338L + V364I | *** | *** | *** | *** | *** | *** |
| A262H + A338V + V364I + A158P | **** | *** | *** | *** | **** | *** |
| A262H + A338V + V364I + A158V | *** | **** | *** | **** | **** | *** |
| A262H + A338V + V364I + A158P + I159N | ***** | **** | **** | **** | **** | **** |
| A262H + A338V + V364I + A158V + I159N | ***** | ***** | ***** | ***** | **** | **** |

The selectivity e.e. of the S-type product was represented by *, and the selectivity of the female parent and its equivalent mutant was represented by "—", and it was 0-5%.
* represented that e.e. was 5-10%,
** represented that e.e. was 15%-20%,
*** represented that e.e. was 20-50%,
**** represented that e.e. was 50-80%, and
***** represented that e.e. was ≥80%.

Embodiment 4

10 mg/100 mg of Substrate 2/Substrate 3/Substrate 6 were taken respectively, and 1 mg of resuspended lipase or its mutant bacterial sludge was added to a reaction system, 0.3 M pH 7.5 KPB Buffer was supplemented to 1000 μL of the system, and it was reacted at a constant temperature of 30° C. for 1 h at 200 rpm. 60 μL of 6 M diluted hydrochloric acid was added to the system and the reaction was terminated after being mixed uniformly, then 1 mL of n-hexane was added for extraction, it was shaken fully, and centrifuged at 12000 rpm for 2 min, and an upper layer was taken and sent to a sample bottle for detecting the e.e. value of an S-type product by a normal phase HPLC. 3 better mutants were selected and gradually amplified from 10 mg to 100 mg and then to 1 g, the e.e. values of the S-type product were all significantly improved. The specific reaction characteristics were shown in Table 4.

TABLE 4

| Mutant | | | Female parent | A262H + A338V + V364I | A262H + A338V + V364I + A158V | A262H + A338V + V364I + A158P + I159N |
|---|---|---|---|---|---|---|
| Selectivity | Substrate 2 | 10 mg | — | **** | **** | ***** |
| | | 100 mg | — | **** | **** | ***** |
| | | 1 g | — | **** | **** | ***** |
| | Substrate 3 | 10 mg | — | **** | **** | **** |
| | | 100 mg | — | **** | **** | **** |
| | | 1 g | — | **** | **** | **** |
| | Substrate 6 | 10 mg | — | **** | ***** | **** |
| | | 100 mg | — | **** | ***** | **** |
| | | 1 g | — | **** | ***** | **** |

The selectivity e.e. of the S-type product was represented by *, and "—" represented that the selectivity of the female parent was 0-5%.
* represented that e.e. was 5-10%,
** represented that e.e. was 15%-20%,
* represented that e.e. was 20-50%, ** represented that e.e. was 50-80%, and
***** represented that e.e. was ≥80%.

Embodiment 5

10 mg of Substrate 2/Substrate 5 were taken respectively, and resuspended lipase or its mutant bacterial sludge was sequentially added to a reaction system. 0.3 M pH 7.5 KPB Buffer was supplemented to 1000 μL of the system, it was reacted at different reaction temperatures of 15° C./20° C./30° C. for 1 h at 200 rpm, and the effects of the temperatures on selectivity of an S-type product were investigated.

In addition, DMSO, acetone, dimethyltetrahydrofuran, isopropanol, and n-propanol with volume percentages of 5% and 10% were added to the system, and 0.3 M pH 7.5 KPB Buffer was supplemented to 1000 μL of the system, it was reacted at a constant temperature of 20° C. for 1 h, and the effects of different additives on the selectivity of the S-type product were investigated. 60 μL of 6 M diluted hydrochloric acid was added to the above system and the reaction was terminated after being mixed uniformly, then 1 mL of n-hexane was added for extraction, it was shaken fully, and centrifuged at 12000 rpm for 2 min, and an upper layer was taken and sent to a sample bottle for detecting the e.e. value of the S-type product by a normal phase HPLC. The specific reaction characteristics were shown in Table 5.

TABLE 5

| / | | Mutant | Female parent | A26H + A38V + V364I | A26H + A38V + V364I + A158V | A26H + A38V + V364I + A158P + I159N |
|---|---|---|---|---|---|---|
| Selectivity | Substrate 2 | 15° C. | — | **** | ***** | ***** |
| | | 20° C. | — | ***** | **** | ***** |
| | | 30° C. | — | **** | **** | ***** |
| | | 5% DMSO | — | **** | **** | **** |
| | | 10% DMSO | — | **** | **** | ***** |
| | | 5% acetone | — | **** | **** | **** |
| | | 10% acetone | — | **** | **** | **** |
| | | 5% dimethyltetrahydrofuran | — | ***** | **** | ***** |
| | | 10% dimethyltetrahydrofuran | — | ***** | ***** | **** |
| | | 5% isopropanol | — | **** | **** | **** |
| | | 10% isopropanol | — | **** | **** | ***** |
| | | 5% n-propanol | — | **** | **** | **** |
| | | 10% n-propanol | — | **** | **** | **** |

TABLE 5-continued

| / | | Mutant | Female parent | A26H + A38V + V364I | A26H + A38V + V364I + A158V | A26H + A38V + V364I + A158P + I159N |
|---|---|---|---|---|---|---|
| | Substrate 5 | 15° C. | — | *** | **** | **** |
| | | 20° C. | — | **** | *** | **** |
| | | 30° C. | — | *** | *** | **** |
| | | 5% DMSO | — | *** | *** | *** |
| | | 10% DMSO | — | *** | *** | **** |
| | | 5% acetone | — | *** | *** | *** |
| | | 10% acetone | — | *** | *** | *** |
| | | 5% dimethyltetrahydrofuran | — | **** | *** | **** |
| | | 10% dimethyltetrahydrofuran | — | **** | **** | *** |
| | | 5% isopropanol | — | *** | *** | *** |
| | | 10% isopropanol | — | *** | *** | **** |
| | | 5% n-propanol | — | *** | *** | *** |
| | | 10% n-propanol | — | *** | *** | *** |

The selectivity e.e. of the S-type product was represented by *, and "—" represented that the selectivity of the female parent was 0-5%.
* represented that e.e. was 5-10%,
** represented that e.e. was 15%-20%,
*** represented that e.e. was 20-50%,
**** represented that e.e. was 50-80%, and
***** represented that e.e. was ≥80%.

From the above description, it may be seen that the above embodiments of the present disclosure achieve the following technical effects: the amino acid sequence of the lipase shown in SEQ ID NO: 1 undergoes the rational design and a series of evolutionary screening, to obtain the lipase mutants with structural and functional changes, and these lipase mutants generate the S-type product with the significantly improved stereoselectivity e.e. value when used for the catalytic reaction, so that it is almost impossible to selectively produce the S-type product by using the enzyme catalyzed method initially, but under a certain conversion rate, the S-type product with the selectivity at least greater than 80% may be obtained, it meets the needs of industrial production to a great extent.

The above are only preferred embodiments of the present disclosure and are not intended to limit the present disclosure. For those skilled in the art, the present disclosure may have various modifications and variations. Any modifications, equivalent replacements, improvements and the like made within the spirit and principles of the present disclosure shall be included within the scope of protection of the present disclosure.

What is claimed is:

1. A lipase mutant, wherein the lipase mutant comprises:

1) A protein having the amino acid sequence of SEQ ID NO: 1 with a mutation of one or more amino acids selected from the group consisting of:

| | |
|---|---|
| A262H | |
| A338V | |
| V364I | A262H + A338V + V364I + L65I |
| A158P | A262H + A338V + V364I + P243K |
| A158V | A262H + A338V + V364I + F66Y |
| I159N | A262H + A338V + V364I + A158P + L365Q |
| A262H + A338V | A262H + A338V + V364I + A158P + N263G |
| A262H + A338V + V364I | A262H + A338V + V364I + A158P + C68S |
| A262H + A338V + V364I + A158P | A262H + A338V + V364I + A158P + C68Y |
| A262H + A338V + V364I + A158V | A262H + A338V + V364I + A158P + L365V |
| A262H + A338V + V364I + A158P + I159N | A262H + A338V + V364I + A158P + Y363M |
| A262H + A338V + V364I + A158V + I159N | A262H + A338V + V364I + A158P + P336G |
| A262H + A338F | A262H + A338V + V364I + A158P + S67P |
| A262H + A338L | A262H + A338V + V364I + A158P + V226I |
| A262H + I245W | A262H + A338V + V364I + A158P + V226W |
| A262H + I245H | A262H + A338V + V364I + A158P + T236R |
| A262H + I245S | A262H + A338V + V364I + A158P + L365T |
| A262H + I245C | A262H + A338V + V364I + A158V + L365Q |
| A262H + S67R | A262H + A338V + V364I + A158V + N263G |
| A262H + A338V + A158P | A262H + A338V + V364I + A158V + C68S |
| A262H + A338V + A158V | A262H + A338V + V364I + A158V + C68Y |
| A262H + A338V + R123K | A262H + A338V + V364I + A158V + L365V |
| A262H + A338V + H262E | A262H + A338V + V364I + A158V + Y363M |
| A262H + A338V + V364H | A262H + A338V + V364I + A158V + P336G |
| A262H + A338V + R237F | A262H + A338V + V364I + A158V + S67P |
| A262H + A338V + G337A | A262H + A338V + V364I + A158P + L365Q + I159N |
| A262H + A338V + V364L | A262H + A338V + V364I + A158P + N263G + I159N |
| A262H + A338V + T236N | A262H + A338V + V364I + A158P + C68S + I159N |
| A262H + A338V + V364F | A262H + A338V + V364I + A158P + C68Y + I159N |
| A262H + A338V + H262Y | A262H + A338V + V364I + A158P + L365V + I159N |

-continued

| | |
|---|---|
| A262H + A338V + V364I + I245W | A262H + A338V + V364I + A158P + Y363M + I159N |
| A262H + A338V + V364I + I159Y | A262H + A338V + V364I + A158P + P336G + I159N |
| A262H + A338V + V364I + I159F | A262H + A338V + V364I + A158P + S67P + I159N |
| A262H + A338V + V364I + V364L | A262H + A338V + V364I + A158P + V226I + I159N |
| A262H + A338V + V364I + A244I | A262H + A338V + V364I + A158P + V226W + I159N |
| A262H + A338V + V364I + I245D | A262H + A338V + V364I + A158P + T236R + I159N |
| A262H + A338V + V364I + L65T | A262H + A338V + V364I + A158P + L365T + I159N |
| A262H + A338V + V364I + T160L | A262H + A338F + V364I |
| A262H + A338V + V364I + P243M | A262H + A338L + V364I |

and the protein has an amino acid sequence with at least 98% identity to the amino acid sequence of SEQ ID NO:1.

2. The lipase mutant according to claim 1, the protein in 2) has an amino acid sequence with more than 99% identity to the amino acid sequence of the protein in 1), and the lipase mutant is obtained from *Pseudomonas putida* and has the lipase activity.

3. The lipase mutant according to claim 1, the protein in 2) has an amino acid sequence with more than 99.5% identity to the amino acid sequence of the protein in 1), and the lipase mutant is obtained from *Pseudomonas putida* and has the lipase activity.

4. A DNA molecule, wherein the DNA molecule encodes the lipase mutant according to claim 1.

5. A recombinant plasmid, wherein the recombinant plasmid comprises the DNA molecule according to claim 4.

6. The recombinant plasmid according to claim 5, wherein the recombinant plasmid is selected from any one of the following: pET-21b(+), pET-22b(+), pET-3a(+), pET-3d(+), pET-11a(+), pET-12a(+), pET-14b, pET-15b(+), pET-16b (+), pET-17b(+), pET-19b(+), pET-20b(+), pET-21a(+), pET-23a(+), pET-23b(+), pET-24a(+), pET-25b(+), pET-26b (+), pET-27b(+), pET-28a(+), pET-29a(+), pET-30a(+), pET-31b(+), pET-32a(+), pET-35b(+), pET-38b(+), pET-39b(+), pET-40b(+), pET-41a(+), pET-41b(+), pET-42a(+), pET-43a (+), pET-43b(+), pET-44a(+), pET-49b(+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwin1, pEZZ18, pKK232-8, pUC-18 and pUC-19.

7. A non-plant host cell, wherein the host cell comprises the recombinant plasmid according to claim 5.

8. The host cell according to claim 7, wherein the host cell is a prokaryotic cell or a eukaryotic cell, and the eukaryotic cell is a yeast cell.

9. The host cell according to claim 7, wherein the host cell is a competent cell.

10. The host cell according to claim 9, wherein the competent cell is an *Escherichia coli* BL21 cell or an *Escherichia coli* W3110 cell.

11. A method for preparing a chiral compound, wherein the method comprises:

using the lipase mutant according to claim 1 to catalyze hydrolysis of an ester compound shown in Formula I into an acid compound shown in Formula II and an alcohol compound shown in Formula III:

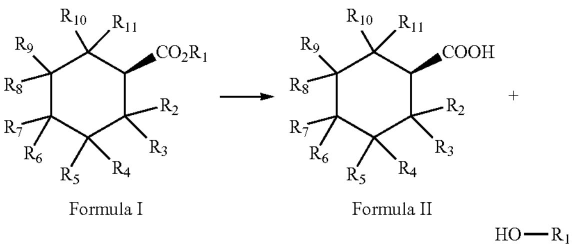

Formula I

Formula II

Formula III wherein, $R_1$ is selected from any one of the following: $CH_3$, $CH_2CH_3$, $CH_2—CH_2CH_3$, or $CHCH_3CH_3$;

$R_2$, $R_3$, $R_4$, and $R_5$ are each independently selected from any one of the following: H, F, Cl, Br, I, OH, $CH_3$, or $CH_2CH_3$; and the presence or absence of a double bond in a cyclohexane ring, when it is present, the double bond forms at any one or more of the following sites: between $R_3$ and $R_4$, between $R_5$ and $R_6$, between $R_7$ and $R_5$, and between $R_9$ and $R_{10}$.

12. The method according to claim 11, wherein the ester compound is selected from any one of the following:

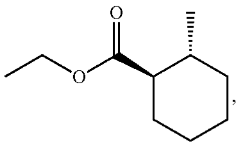
,
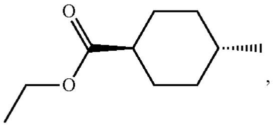
,
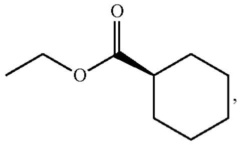
,
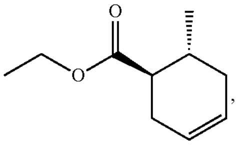
,
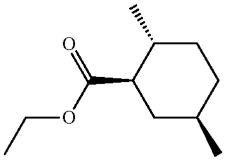
and
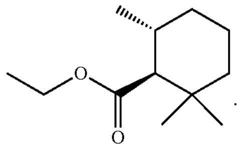
.

13. The method according to claim 11, wherein the lipase mutant catalyzes a hydrolysis reaction of the ester compound shown in Formula I at a temperature of 15° C.~30° C.

14. The method according to claim 11, wherein a mass ratio of a bacterial sludge amount of the lipase mutant to the ester compound is 1:10~1:1.

15. The method according to claim 11, wherein a reaction system comprises an organic solvent, and the organic solvent is selected from any one of the following: dimethylsulfoxide (DMSO), acetone, dimethyltetrahydrofuran, isopropanol, and n-propanol.

16. The method according to claim 15, wherein a volume percentage content of the organic solvent in the reaction system is 5%~10%.

* * * * *